(12) United States Patent
Simpson et al.

(10) Patent No.: US 10,457,912 B2
(45) Date of Patent: Oct. 29, 2019

(54) STROMAL VASCULAR FRACTION PROCESSING DEVICES AND METHODS

(71) Applicant: FLEX PARTNERS, Solana Beach, CA (US)

(72) Inventors: Philip J. Simpson, Escondido, CA (US); David G. Matsuura, Del Mar, CA (US); Darryl D'Lima, San Diego, CA (US); Daniel Kincade, Encinitas, CA (US)

(73) Assignee: FLEX PARTNERS

( * ) Notice: Subject to any disclaimer, the term of this patent is extended or adjusted under 35 U.S.C. 154(b) by 405 days.

(21) Appl. No.: 15/512,470

(22) PCT Filed: Sep. 18, 2015

(86) PCT No.: PCT/US2015/051043
§ 371 (c)(1),
(2) Date: Mar. 17, 2017

(87) PCT Pub. No.: WO2016/044780
PCT Pub. Date: Mar. 24, 2016

(65) Prior Publication Data
US 2017/0292110 A1    Oct. 12, 2017

Related U.S. Application Data

(60) Provisional application No. 62/053,011, filed on Sep. 19, 2014.

(51) Int. Cl.
*G01N 1/00* (2006.01)
*C12N 5/071* (2010.01)
*C12M 1/00* (2006.01)
*A61B 10/00* (2006.01)
*B01D 21/00* (2006.01)
(Continued)

(52) U.S. Cl.
CPC ........ *C12N 5/0602* (2013.01); *A61B 10/0096* (2013.01); *B01D 21/0012* (2013.01); *B01D 21/262* (2013.01); *C12M 41/48* (2013.01); *C12M 47/04* (2013.01); *C12Q 3/00* (2013.01); *C12N 2509/00* (2013.01)

(58) Field of Classification Search
CPC .......................................................... G01N 1/00
See application file for complete search history.

(56) References Cited

U.S. PATENT DOCUMENTS

2011/0054347 A1   3/2011   Goss et al.
2012/0276628 A1   11/2012  Khan et al.
(Continued)

FOREIGN PATENT DOCUMENTS

WO    WO-2014/039697 A1    3/2014

*Primary Examiner* — Jyoti Nagpaul
(74) *Attorney, Agent, or Firm* — Mintz Levin Cohn Ferris Glovsky and Popeo, P.C.

(57) ABSTRACT

Disclosed herein are systems, devices and methods for processing tissue, such as autologous tissue. Implementations of a Stromal Vascular Fraction (SVF) system are described that can isolate and wash harvested cells contained within various tissues, such as isolate and wash stem cells from fat tissue. The SVF system can minimize the handling and transferring of tissue and fluids, including minimizing the number of human interventions and manipulations required throughout processing. The SVF system can ensure sterility of processed tissue and harvested cells, as well as significantly reduce cost and time associated with the processing.

31 Claims, 16 Drawing Sheets

(51) Int. Cl.
*B01D 21/26* (2006.01)
*C12M 1/36* (2006.01)
*C12Q 3/00* (2006.01)

(56) References Cited

U.S. PATENT DOCUMENTS

| | | |
|---|---|---|
| 2012/0283563 A1 | 11/2012 | Moore et al. |
| 2013/0012921 A1 | 1/2013 | Pustilnik et al. |
| 2013/0324966 A1 | 12/2013 | Park et al. |
| 2014/0094930 A1 | 4/2014 | Nash et al. |

STROMAL VASCULAR FRACTION PROCESSING DEVICES AND METHODS

CROSS-REFERENCE TO RELATED APPLICATION

The current application is a national stage entry, filed under 35 U.S.C. § 371, of International Application No. PCT/US2015/051043, filed on Sep. 18, 2015, and claims priority to U.S. provisional patent application Ser. No. 62/053,011, filed on Sep. 19, 2014 and entitled "Stromal Vascular Fraction Processing Devices and Methods," which are incorporated by reference herein in their entireties.

TECHNICAL FIELD

The subject matter described herein relates to devices, systems and methods for Stromal Vascular Fraction (SVF) processing.

BACKGROUND

Concentrated autologous stem cells can have therapeutic value for a variety of conditions. The process of Stromal Vascular Fraction (SVF) is the separation of cells (such as stem cells, progenitor cells, and other stromal cells) from a matrix of autologous tissue in which they are present. The cells in the SVF can have therapeutic applications against a variety of diseases. A complicated process can be required in order to isolate stem cells from autologous tissue, which can be obtained from a patient by means of liposuction, a syringe extraction procedure, or other surgical techniques. For example, the process of isolating and preparing stem cells for subsequent use can require significant equipment and several steps, including multiple fluid transfers. Such processes can make it difficult to maintain a sterile environment for the stem cells, which can result in high costs and long processing times with lower yields.

SUMMARY

Aspects of the current subject matter can include devices, systems and methods for processing tissue samples. In one aspect, a tissue processing system is described that includes a processing device having an outer housing that contains an inner compartment and a containment device that includes an outer body that releasably couples to the inner compartment of the processing device. The containment device can include a transfer line that has a hollow passageway that extends a distance along a center axis of the outer body. In addition, the containment device can include at least one chamber in fluid communication with the transfer line and positioned within the outer body and a collection chamber releasably coupled to a collection port contained within the outer body. The collection chamber can be in fluid communication with the transfer line. Additionally, the containment device can include a shuttle valve including a transfer pathway that extends through the shuttle valve, with the shuttle valve being moveable along the transfer line for creating, depending upon a position of the shuttle valve along the transfer pathway, a fluid pathway between two chambers of the at least one chamber or between a chamber of the at least one chamber and the collection chamber.

In some variations one or more of the following features can optionally be included in any feasible combination. For example, the containment device can include a first chamber of the at least one chamber, with the first chamber having a filter that partitions the first chamber into a first sub-chamber and a second sub chamber. The first sub-chamber can be positioned closer to the center axis than the second sub-chamber. The second sub-chamber can be in fluid communication with the transfer line. The first sub-chamber can be in fluid communication with a port that extends through the outer body. The port can be coupled to a tissue collection device. The second sub-chamber can be in fluid communication with the collection chamber when the shuttle valve is positioned along the transfer line such that the transfer pathway is in fluid communication with the second sub-chamber and the collection chamber. The shuttle valve can include a passive valve along the transfer pathway that controls the direction of fluid or material through the shuttle valve. The filter can allow the passage of stem cells and prevent the passage of fat tissue through the filter. The first chamber can include at least one of a passive feature and an active feature for at least one of breaking-up, mixing, inducing turbulence, and inducing agitation to contents contained in the first chamber. At least one of the collection chamber, the one or more chambers, and the transfer pathway can include a surface coating that influences the retention or rejection of at least one of a specific chemical and a specific biological material. The collection chamber can include a plunger and a spring that applies a spring force against the plunger. The spring force can be less than a centrifugal force of the plunger when the containment device rotates during centrifugation thereby allowing the plunger to compress the spring and create a vacuum in the collection chamber. The vacuum can force contents into the collection chamber from one or more of the at least one chamber and the collection chamber depending upon the position of the shuttle valve. The processing device can include a control panel in communication with a processor for programming one or more tissue processes to be completed by the tissue processing system. The processing device can include a sensor that collects sensed data, and the processor can process the sensed data for determining a processing feature of the containment device during the one or more tissue processes. The processor can process the sensed data in real-time. The processing feature can include at least one of a rotational speed of the containment device, a rate of collection of sample tissue into the first sub-chamber, and a temperature in the containment device. The collection chamber can include a syringe.

In another interrelated aspect of the current subject matter, a method includes allowing a coupling of a containment device of a tissue processing system to an inner compartment of a processing device of the tissue processing system and allowing a loading of a tissue sample and a solution in a first sub-chamber of a first chamber of the containment device, with the first chamber including a filter that divides the first chamber into the first sub-chamber and a second sub-chamber. In addition, the method can include agitating the containment device to assist with mixing the tissue sample and the solution and moving a shuttle valve positioned along a transfer line that extends a distance within an outer body of the containment device, with the shuttle valve including a transfer pathway that extends through the shuttle valve. Additionally, the method can include positioning the shuttle valve such that the transfer pathway creates a first fluid pathway between the second sub-chamber and a collection chamber releasably coupled to a collection port within the containment device. The method can further include rotating the containment device along a center axis of the containment device to centrifuge the tissue sample and solvent and allowing a first type of cell comprising the tissue sample to pass through the filter and collect in the second sub-chamber. Furthermore, the method can include creating, during rotation of the containment device, a vacuum in the collection chamber thereby drawing the stem cells into a volume within the collection chamber, the vacuum created as a result of the rotation of the containment device.

In some variations one or more of the following can optionally be included in any feasible combination with the method. For example, in one aspect the method can further include allowing the removal of at least one of the containment device and the collection chamber from the processing device. In addition, the first type of cells can be stem cells. The creating the vacuum can further include allowing a plunger acting upon a spring in the collection chamber to overcome the spring force of the spring with a centrifugal force of the plunger thereby moving the plunger and compressing the spring. The first sub-chamber can be positioned closer to the center axis than the second sub-chamber and the first sub-chamber can be in fluid communication with a port that extends through the outer body. The port can be coupled to a tissue collection device. Additionally, the method can further include programming, based on an input from a control panel of the processing device, the tissue processing system to perform a tissue process on the tissue sample, wherein the processing device includes a processor in communication with the control panel. In addition, the method can further include processing, by the processor, sensed data collected by a sensor of the processing device and adjusting a processing feature of the containment device based on the processed sensed data. The processor can process the sensed data in real-time and the processing feature can include at least one of a rotational speed of the containment device, a rate of collection of the tissue sample into the first sub-chamber, and a temperature in the containment device.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Figures 1, 2:
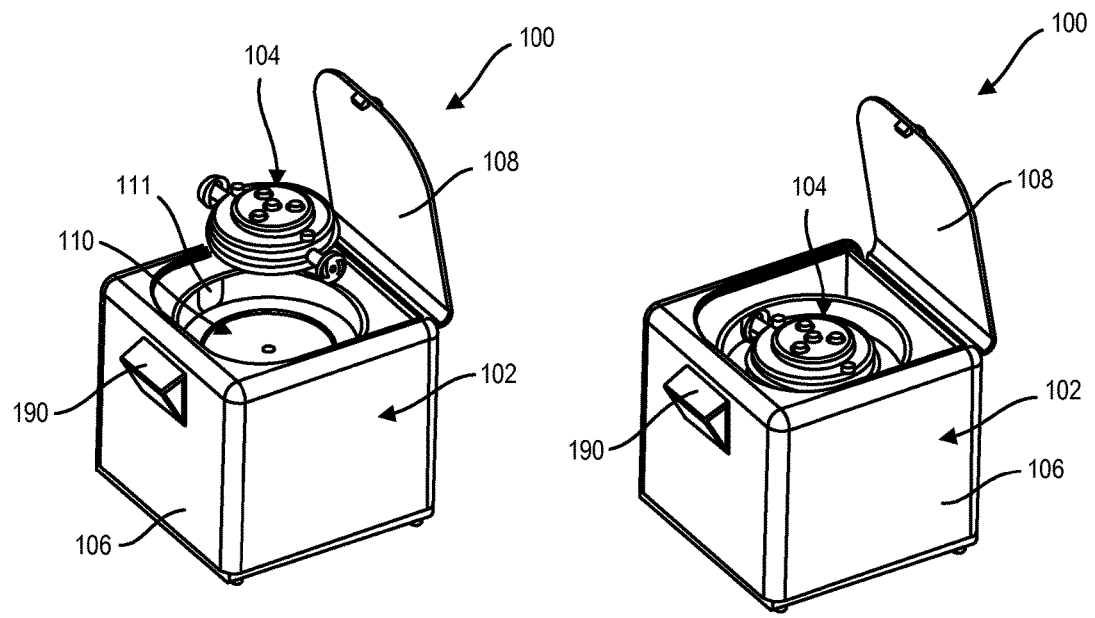
FIG. 1 is a perspective view of an embodiment of Stromal Vascular Fraction (SVF) system including a containment device and a processing device, with the containment device shown decoupled from the processing device.
FIG. 2 is a perspective view of the SVF system of FIG. 1 with the containment device shown coupled to the processing device.

The present disclosure describes embodiments of a Stromal Vascular Fraction (SVF) system that can be used for containing and processing tissue in a more time and cost efficient way. Additionally, the SVF system can provide improved sterile environments for the tissue, such as during storage and processing by limiting the transfer of fluids and tissue to exposed environments. The SVF processing system can also reduce human error by being automated.

In some implementations, the SVF system can include a containment device and a processing device, with the processing device being reusable and configured to house and manipulate the containment device, which can be disposable. The processing device can provide programmed or programmable processes, such as agitation, centrifugal separation, temperature control, heating, incubation, and valve actuation. Programming of the processing device can be accomplished, for example, automatically through the use of pre-programmed RFID or bar code tags associated within the containment device. Alternatively, programming can be accomplished manually, such as by a user using a keypad or graphical user interface (e.g., touch pad or control panel) associated with the processing device.

The containment device, which can be provided in a sterilized state, can be configured to house and protect the sterility of a tissue sample and other fluids at least throughout processing. The containment device can include a plurality of chambers, which can be configured to contain fluids, material, etc. In addition, the containment devices can include passive valves and active valves that can be activated in order to allow either movement or manipulation of contents within the chambers, such as during execution of programmed processes. This can assist with yielding processed harvested cells, such as stem cells, that can be ready for reintroduction into a patient or storage for future use.

The chambers of the containment device can be in communication with one or more ports that can allow for filling the chambers with tissue (such as autologous tissue) and/or fluids. In addition or alternatively, the one or more ports can be configured to allow for the removal of contents within the chambers. The ports can also assist with providing a sterile barrier for protecting the contents of the chambers from contaminants. For example, the ports can be hydrophilic, including vents, and/or include filters. The chambers can contain and manipulate any number of a variety of materials and/or fluids (e.g., solvents, pharmaceuticals, etc.). In addition, for example, the chambers can be used to wash tissue, collect waste, and collect and isolate refined stem cells. Any one of the chambers (or other collection features, such as syringes associated with the collection device) and/or fluid passageways within the containment device can include a surface treatment or coating. The surface treatment or coating can influence the retention or rejection of either a specific chemical or a specific biological material, which can assist with tissue processing. In addition, any one of the chambers or collection chambers can include a passive or active feature for assisting with breaking up, mixing, and/or inducing agitation to the contents contained therein, which can also assist with tissue processing.

In some implementations of the SVF system, a primary valve (such as a shuttle valve) can be controlled either manually or by the processing device to facilitate moving fluids and/or material from chamber to chamber, including one or more times throughout a programmed process in order to facilitate, mixing, washing, separating, and/or isolating chamber contents. The containment device can also include other valves that are passive (e.g., check valves) or valves that are actuated by other means.

The SVF system can also be configured to allow for isolating small volumes of stem cells, such as for the purpose of removing cells or preventing re-dilution or contamination of cells with other fluids. The contents of the chambers can remain sterile at least throughout processing, including during valve activation, transferring fluid, and accessing chambers. Caps, self-closing ports and other sterile barriers can be used for access ports and vents to assist with maintaining sterility.

In some embodiments, the containment device can include three chambers. For example, the containment device can include a diluent chamber for washing solution, a waste chamber for containing waste, and a processing chamber that can contain stem cells. There can be more than three chambers for the same or similar processing, as well as other purposes in other embodiments. For example, in some implementations, a tissue collecting chamber can include a blender or similar features for breaking apart tissue captured in the tissue collecting chamber. In addition, the chambers can be arranged in any configuration that facilitates processing of tissue. For example, the chambers can be placed radially, including evenly spaced, about a center of rotation (i.e., center axis), in line, and/or parallel to each other. In some embodiments, one or more chambers can be contained within other chambers or placed on top of each other. The chambers can be of any shape or configuration, however a cylindrical shape can be preferred, such as when using conventional sealing methods.

The layout of the chambers can be driven by overall size of the containment device, location and access to valving components, centrifugal forces available to facilitate fluid movement, and user convenience. Some embodiments can include a "pocket" located within a piston or plunger of a syringe of the containment device, which can be allow for the collection of small amounts of stem cells during processing. Chambers can also include collapsible features, such as a bellow, diaphragm, flaccid bag-like construction, or any feature made of elastomeric materials that can store kinetic energy that can be used to assist in the transfer of materials. Some chambers, including chambers configured as syringes, can include features for actively dispensing contents therefrom, such as pneumatic or hydraulic features that control movement of a plunger or piston. The controlled movement can also be independent of a rotation or movement of the containment device. Alternatively or in addition, such plungers or pistons can be activated as a result of movement, such as rotation, of the containment device, as will be discussed for example in greater detail below. The chambers may also be coated to prevent adhesion of fluids and/or materials, and to minimize transfer of fluids and/or materials (such as extractables) from chamber walls.

Energy required to move fluids and/or material between chambers can be supplied by the processing device, such as in the form of centrifugal force. For example, spinning of the processing device coupled with a system of weighted pistons or plungers, valves, and strategically sized chambers can allow movement of fluids at programmed times (and optionally at programmed speeds) between the chambers, including sequentially throughout processing. In addition, chambers can include syphons that can assist with drawing fluid and/or materials out of the chambers, such as for transferring to another chamber and/or syringe.

Programmed activation of the valves within the containment device can control the movement of the fluids within and between chambers. For example, in some embodiments, a main spool or shuttle valve can be mechanically operated by the processing device that can be centrally located relative to the center axis of rotation such that it can be actuated during a dynamic centrifugal cycle. Other valving can be passive, such as duckbill or spring loaded check valves. Valves may also be activated based on a rotation speed or centrifugal force, or by other mechanical, magnetic, pneumatic, or hydraulic mechanisms. As such, by varying the rotational speed of the containment device (including starting and stopping rotation), one or more valves can be actuated and the transfer of fluid and/or material between one or more chambers and/or syringes of the containment device can be controlled.

In addition, the processing device and/or the containment device can contain active or passive balancing devices to facilitate the redistribution of the fluids moving from chamber to chamber during processing, as well as to reduce vibration of the SVF system.

One or more sensors and other electronic monitoring equipment can be included in the processing device and/or the containment device to initiate automated functions within a processing cycle, and/or to determine a snap-shot condition of the fluids or cells during processing. For example, sensors can include one or more of the following features: electronic, optical, magnetic, RF, mechanical, position sensing, temperature sensing, etc. One or more sensors can be used to determine or quantify a variety of conditions, such as clarity, cell count, temperature, speed, position, cologenase, blood, specific gravity, balance, etc. In addition, one or more sensors can monitor turbidity, such as during a wash cycle in order to adapt a volume or number of rinse cycles. The sensors can be in communication with a processor of the processing device, which can process sensed data collected by the sensor, including in real-time. This can allow the processing device, via the processor, to control one or more settings associated with the SVF system, such as for controlling the contents and/or outcome of the tissue processing. For example, the processor can collect sensed temperature data from a temperature sensor in order to determine whether to increase or decrease the temperature in a part of the containment device, such as within a chamber of the containment device that contains temperature sensitive cells.

In some embodiments, one or more filters can be used to filter out particles larger than cells and debris smaller than cells in order to enhance cell enrichment during processing. Hydrophobic membranes can be used, such as to facilitate sterile venting of the chambers. In addition, other types of filters and material can be used for processing (e.g. lipid or hydrophilic filters, stainless steel mesh, etc.).

Cells can be automatically detected and counted using the SVF processing system, for example using an optical sensor, during various stages of processing (e.g., during centrifugation and washing). Cell counting can allow monitoring of the performance of the system, as well as a method of increasing efficiency by halting processing when a desired cell density is reached. For example, the processor can process data collected by the optical sensor in order to determine a cell count. Based on the cell count, the processor can then adjust a setting associated with the SVF system, such as a rotational speed of the containment device or a rate of tissue collection into the containment device. The cell counting method may be combined with a cell morphometry (quantifying cell size and shape, for example) to identify the presence and proportion of different types of cells being harvested.

The chambers and/or fluid pathways within the containment device can be treated or coated with chemicals, such as extracellular matrix proteins. For example such treatments or coatings can encourage certain cell types to adhere to portions of the chambers, thereby removing them from the wash cycle. Alternatively or in addition, the chambers and/or fluid pathways can be treated or coated with chemicals to prevent cells from adhering, thereby keeping cells in suspension.

Although devices, systems, and methods described herein are related to processing tissue, such as autologous tissue, any of the devices, systems, and methods described herein can be used with any of a variety of tissue samples, including non-autologous tissue, and can be used to isolate various constituents of the tissue. For example, the devices, systems, and methods can process any harvested tissue (e.g. bone marrow, fat, etc.), such as for treating and collecting any cell type (e.g., stem cells, progenitor cells, stromal cells, vascular and angiogenic cells, etc.). In addition, the SVF system can be used to collect acellular material, such as for acellular injections (e.g., platelet rich plasma (PRP)). In addition, it is understood that the devices, systems, and methods described herein can be used for veterinary as well as human applications. Furthermore, it is also understood that the devices, systems, and methods described herein can be used for separating and isolating constituents and/or isolating stem cells from any organic material, including plants as well as animal origin. It is understood that some modifications to the process and chemicals described herein may be required depending on either the types of material used with the containment device and/or processing device, or the constituents to be isolated.

FIG. 1 shows an embodiment of the SVF system 100, which includes a processing device 102 and a containment device 104. As shown in FIG. 1, the processing device 102 can include an outer housing 106 with a door or lid 108 that can be opened to receive or remove the containment device 104. The processing device 102 can include an inner compartment 110 that is sized and shaped to accept and releasably couple the containment device 104, such as for processing the contents of the containment device 104. For example, the inner compartment 110 can include a circular-shaped recess, which can allow a containment device 104 having a circular shape to couple to the inner compartment 110, as shown in FIG. 2.

The inner compartment 110 and/or the containment device 104 can include a mating feature 111 that assists with locking or properly aligning the containment device in the inner compartment 110. For example, the outer walls of the inner compartment 110 can include a recess that allows the ends of syringes extending form the containment device 104 to align with such recesses. Once the containment device 104 is coupled to the processing device 102, such as coupled to the inner compartment 110, the door or lid 108 of the processing device 102 can be closed and processing of the contents within the containment device 104 can be commenced. The door 108 of the processing device 102 can remain closed while one or more processes are completed within the SVF system 100. This can assist in providing a sterile environment for the contents of the containment device 104.

Figure 3:
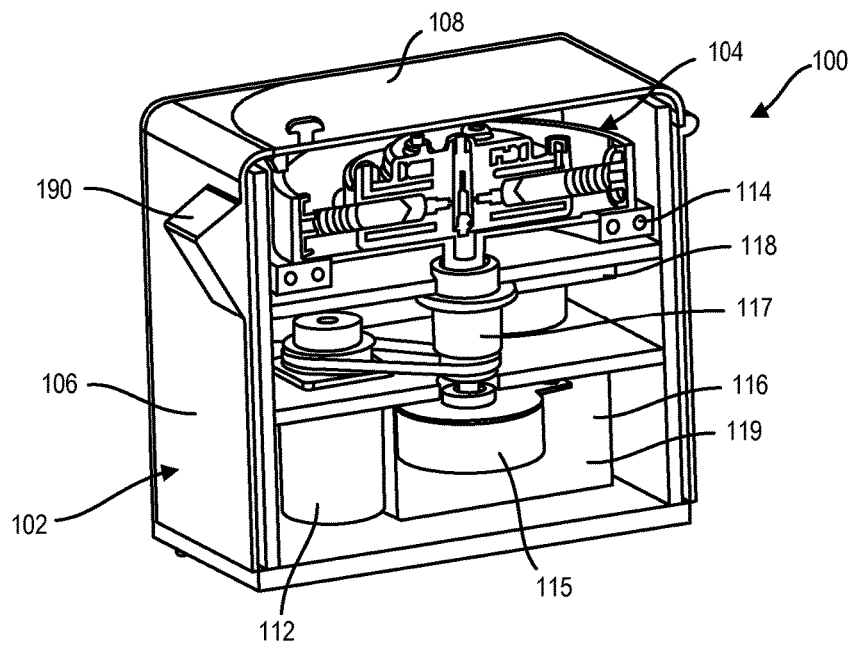
FIG. 3 is a cross-sectional view of the SVF system of FIG. 1.

FIG. 3 shows a cross section view of the SVF system 100, which shows the containment device 104 enclosed within the housing 106 of the processing device 102. As shown in FIG. 3, the processing device 102 can also include a motor 112, a balancing element 114, a clutch 115, temperature and/or motor controller 116, a heater and/or fan assembly 117, sensors 118, a processor 119, and a control panel 190. The motor 112 can assist with performing various processes, such as centrifugation, agitation, etc. The balancing element 114 can be dynamic and assist with reducing vibration during centrifugation, such as by distributing weight radially where needed to reduce vibration. The processor 119 can assist with allowing for programming of the SVF system 100, such as programming various types of processes for the contents of the containment device 104 to undergo. The processor can also be in communication with the control panel 190, such as for allowing a user to program the SVF system and input data. In addition, the processor 119 can be in communication with one or more sensors 118, such as a temperature sensor, pressure sensor, optical sensor (e.g., for measuring fluid clarity), etc. As such, the processor 119 can monitor and process (including in real-time) sensed data collected by the one or more sensors 118 and provide alerts and/or adjust one or more settings associated with the SVF system 100 based on the collected data. For example, the processor 119 can be programmed to adjust a rotational speed of the containment device 104 (i.e., during centrifugation) and/or a number of wash cycles based on an optical density of supernatant fluid, which can be sensed by an optical sensor positioned adjacent the containment device 104.

In some implementations, enzymatic and/or heat treatment of tissue collected in the containment device 104 can be started, such as while tissue is being collected in the containment device 104. The processing device and the temperature controller can assist with such treatments. In some implementations, the amount of tissue collected in the containment device 104 can be monitored, such as by a pressure or optical sensor that is in communication with the processor 119. As such, the processor 119 can monitor the amount of tissue collected and can further control the amount of tissue collected by directing the tissue collecting device (e.g., liposuction device, bone marrow aspirate, etc.) to continue or stop collecting tissue.

Figure 4:
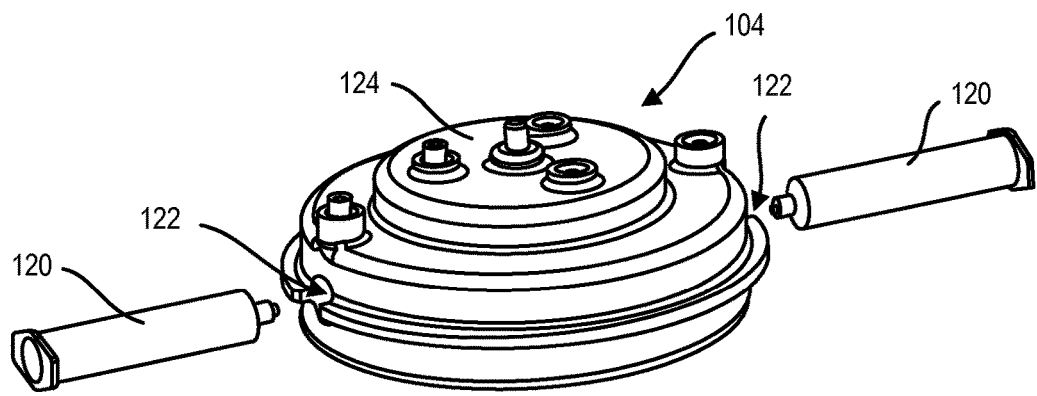
FIG. 4 is an exploded view of the containment device of FIG. 1, which includes a pair of syringes shown removed from respective syringe ports.

FIG. 4 shows an exploded view of an implementation of a containment device 104 showing a pair of collection chambers or syringes 120 removed from their respective collection or syringe ports 122. One or both of the syringes 120 can be used for collecting fluid and/or material, such as a resulting product of a process, as will be discussed in greater detail below. Although the containment device 104 is shown as having two syringes 120 with two respective syringe ports 122, any number of syringe ports 122 for inserting a syringe or collection chamber for the collection and/or delivery of fluids and/or material can be included in the containment device 104. In addition, the syringe ports can be evenly spaced from each other, as shown in FIG. 4, which can assist with balancing the containment device 104, such as during centrifugation.

Figure 5:
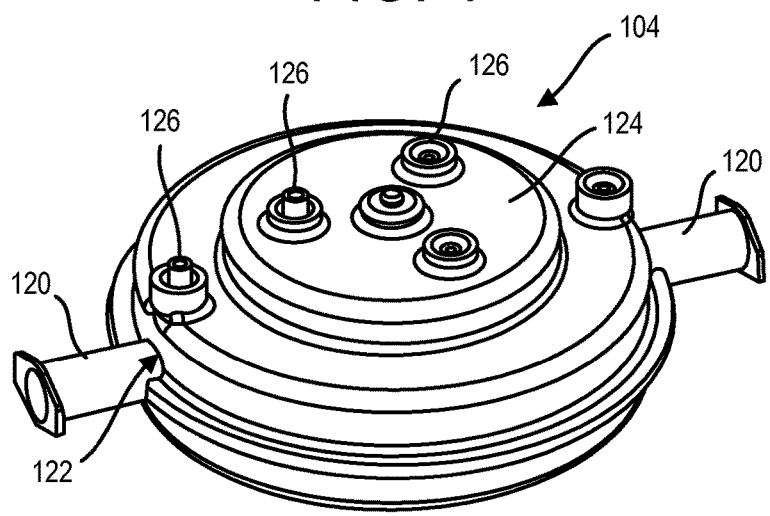
FIG. 5 shows the containment device of FIG. 4 with the syringes are inserted in the syringe ports of the containment device.

FIG. 5 shows the pair of syringes 120 inserted in the syringe ports 122, which can then allow the containment device 104 to be coupled to the inner compartment 110 of the processing device 102. As shown in FIG. 5, the containment device 104 can have an outer body 124 that includes one or more ports 126. Each port 126 can provide fluid communication to a chamber within the containment device 104. Each chamber can accept fluids and/or materials that can be used for processing. For example, the ports 126 can include passive one-way valves that allow a syringe to be coupled to the port 126. Once coupled, such as via a luer lock, the syringe can force a fluid or material past the port 126 and into a respective chamber. The chamber can be sterile and can continue to provide a sterile environment for the fluid or material while in the chamber.

Figure 6A:
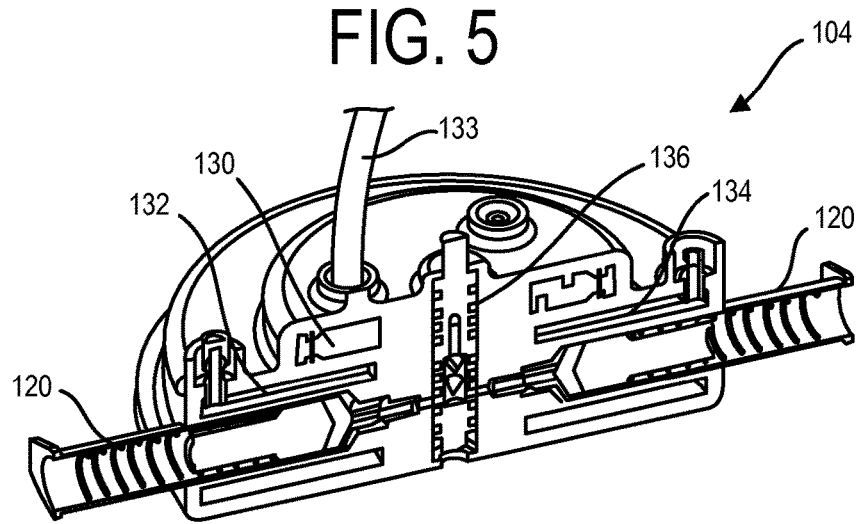
FIG. 6A is a perspective view of a cross-section of the containment device of FIG. 4 showing a transfer line and three chambers.
Figure 6B:
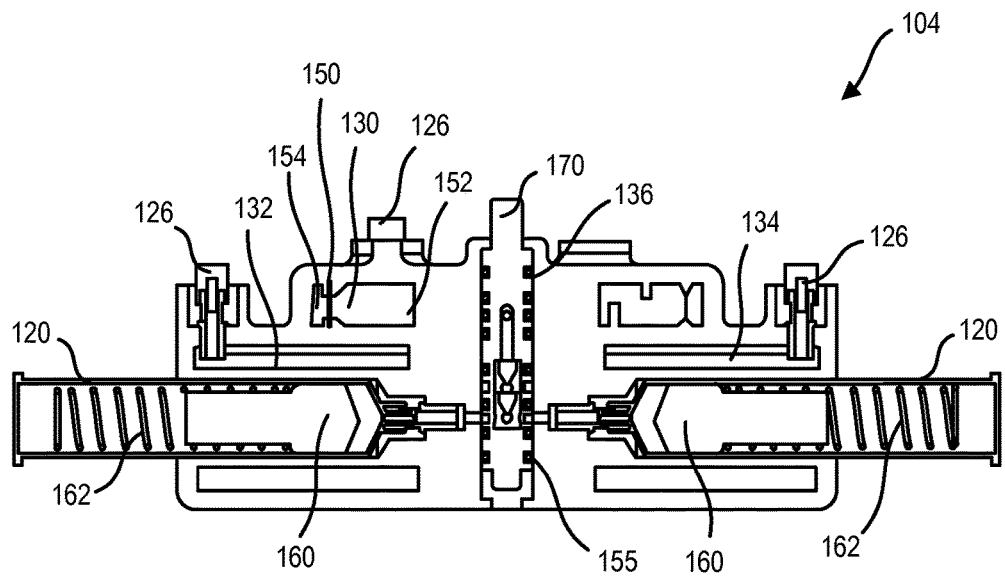
FIG. 6B shows the cross-section view of the containment device of FIG. 6A with the plungers of the syringes in a proximal position.
Figure 6C:
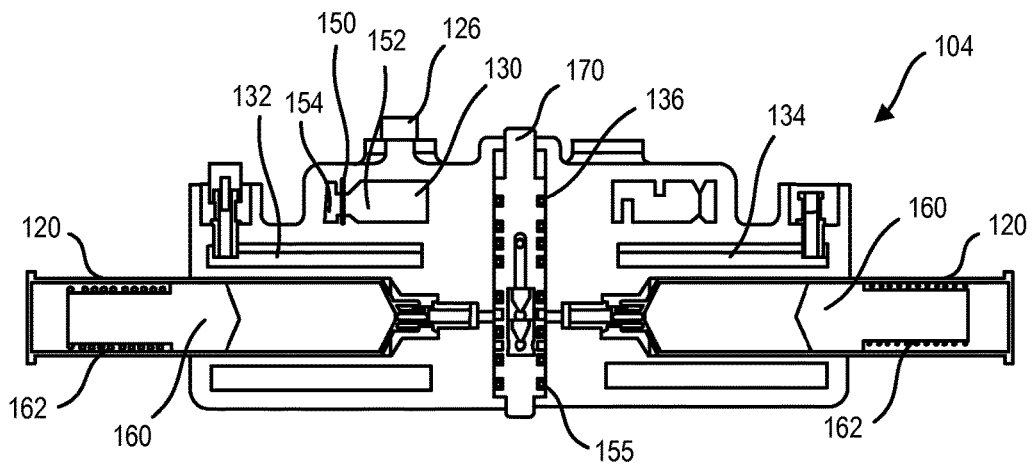
FIG. 6C shows the cross-section view of the containment device of FIG. 6A with the plungers of the syringes in a distal position.

FIGS. 6A-6C shows an implementation of a containment device 104 having a first chamber 130, a second chamber 132, and a third chamber 134, which are all in fluid communication with a transfer line 136. Any number of chambers can be included in the containment device 104 and are not limited to three chambers. Each chamber can provide a sterile compartment for storing fluid and/or material. In addition, the two syringes 120 can also be in fluid communication with the transfer line 136. The transfer line 136 can provide a fluid passageway between any one or more of the chambers (i.e., first chamber, 130, second chamber 132, third chamber 134) and syringes 120.

For example, the first chamber 130 can be configured to accept and store tissue, such as fat cells that have been extracted from a patient. In some implementations, the first chamber 130 can be in direct communication with a tissue collecting device, such as a part of a liposuction device. This can allow for a direct transfer of tissue from the patient to the first chamber 130, which can significantly reduce and minimize the amount of contaminants the tissue would be exposed to.

For example, as shown in FIG. 6A, a tissue collection line 133 can be directly coupled to a port 126 that provides controlled access (such as via a valve) to the first chamber 130. In some implementations, the tissue collection line 133 can be in communication with a vacuum for pulling tissue and/or fluids from a patient, through the tissue line 133, and into the first chamber 130.

The first chamber 130 can include a filter 150 that can assist with separating the contents of the tissue and/or fluid that is placed into the first chamber 130. For example, the filter 150 can prevent or allow the passage of one or more types of fluids and materials through the filter 150. The filter 150 can be located in the first chamber 130 such that it divides the first chamber into a first sub-chamber 152 and a second sub-chamber 154. The first sub-chamber 152 can be in communication with a port 126, such as the port 126 that allows for the introduction of tissue and/or fluids into the first chamber 130. The second sub-chamber 154 can be in communication with a first fluid pathway that extends to the transfer line 136. As such, the fluid and/or material(s) that are allowed to pass through the filter 150 are able to continue on to the transfer line 136. The filter 150 and second sub-chamber 154 can also be positioned closer to the outer circumference of the containment device 104 relative to the first sub-chamber 152. This can allow, for example, during centrifugation, the contents that are allowed to pass through the filter 150 to be forced through the filter 150 and into the second sub-chamber 154. Alternatively or in addition, a vacuum or pressurized air flow can be applied for further assisting with the movement of fluids through the containment device 104.

The second chamber 132 can be used, for example, to store a solvent, such as a rinsing agent or saline. The second chamber 132 can be in fluid communication with the transfer line 136. The second chamber 132 can also be in communication with a port 126, which can be used to either introduce or extract fluid and/or material from the second chamber 132. In addition, the third chamber 134 can be used, for example, to collect and store waste material. The third chamber 134 can also be in fluid communication with the transfer line 136 and a port 126, which can be used to either introduce or extract fluid and/or material from the third chamber 134. Any number of chambers and ports can be included in the containment device 104, and any one of the chambers can be in fluid communication with the transfer line.

Additionally, as shown in FIGS. 6A-6C, the syringes 120 can be in fluid communication with the transfer line 136. Either one or both of the syringes 120 can be filled with a fluid and/or material prior to being loaded into the containment device 104, which can allow the contents to be dispensed during processing. Alternatively or in addition, either one or both of the syringes 120 can be loaded in an empty state, which can allow the syringes 120 to be filled with contents during processing. Any number of syringes 120 can be included in the containment device and can be in fluid communication with the transfer line for either delivering or collecting fluids and/or material.

As shown in FIGS. 6B and 6C, the syringes 120 can include a spring-loaded plunger 160. The spring force of a spring 162 acting against the plunger 160 can allow the plunger 160 to move based on a speed at which the containment device 104 rotates, such as during centrifugation as a result of centrifugal forces. As such, during lower speeds of rotation, the plunger 160 can push against the springs in order to move a smaller distance within the barrel of the syringe 120 (due to lower centrifugal forces acting on the plunger 160). At higher speeds of rotation, the plunger 160 can push against the springs 162 with a greater force, thereby allowing the plunger 160 to move a greater distance within the barrel (due to higher centrifugal forces acting on the plunger 160).

For example, in FIG. 6B, the springs 162 are shown in a fully extended position with the plunger 160 in a proximal position relative to the center axis (or axis of rotation) of the containment device 104. This can be the configuration when the containment device 104 is either not rotating or rotating at a low speed (i.e., zero or low centrifugal forces). FIG. 6C, shows the springs 162 in a fully retracted position with the plunger 160 in a distal position relative to the center axis of the containment device 104. This can be the configuration when the containment device 104 is rotating at a higher speed (i.e., higher centrifugal forces). The speed of rotation of the containment device 104 can therefore control the positioning of the plunger 160 along the respective syringe barrel, which can also control either the dispensing or collecting of fluids and/or material in the syringes 120.

For example, when the containment device 104 is rotating at a high speed, the plunger 160 can be retracted into the distal position, which can create a vacuum in the fluid line that is in communication with the syringe 120. As a result of the created vacuum, fluid and/or material can be drawn into the syringe 120. The syringe 120 along with its contents can then be easily removed from the containment device 120, such as for subsequent storage or use of the contents.

The plunger 160 and spring 162 of a syringe 120 can be configured such that the plunger 160 moves towards the periphery of the containment device 104 upon rotation of the containment device 104, such as shown in FIG. 6C. This can be useful, for example, when the syringe is used for collecting fluids and/or material during processing. However, the plunger 160 and spring 162 can be configured such that the plunger 160 moves towards the center of the containment device 104 upon rotation of the containment device 104, which can force out the contents of the syringe 120. This can be useful, for example, when the syringe 120 is used for delivering fluids and/or material during processing. Although the syringe 120 is described herein as including a spring 120 to act as a resistive element against the plunger 160, any number of resistive elements can be used for allowing the plunger to move either proximally or distally as a result of centrifugal forces acting upon the plunger 160.

The transfer line 136 can allow one or more chambers or syringes 120 to be in fluid communication with each other, as well as assist with transferring fluid(s) and/or material(s) between one or more chambers or syringes. In some implementations, each of the chambers and syringes are in direct fluid communication with the transfer line 136. However, any of the chambers and/or syringes can include a valve that controls the flow of fluid to and from the transfer line 136, such as a passive valve (e.g., one-way valves, etc.).

Figure 7A:
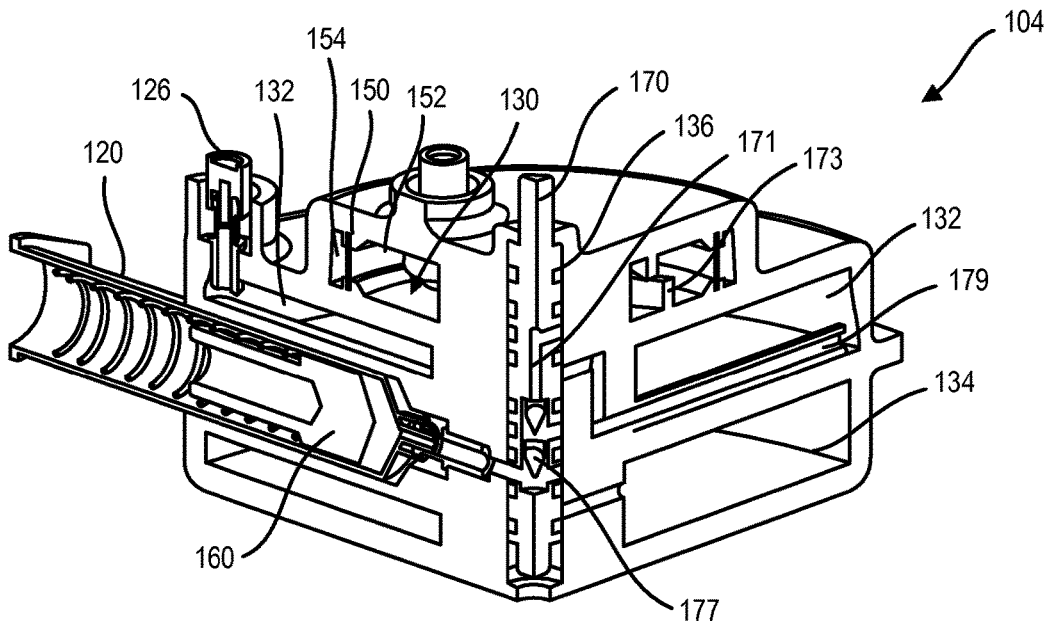
FIG. 7A is a perspective view of a section of the containment device of FIG. 4 showing a shuttle valve having a transfer pathway that is positioned along the transfer line.

In some implementations, the transfer line 136 can include a shuttle valve 170 that can control the flow of fluid and/or materials between the one or more chambers and syringes. For example, as shown in FIG. 7A, the shuttle valve can include one or more transfer pathways 172 that, when aligned with one or more fluid pathways in communication with one or more chambers and/or syringes, can allow fluids and/or materials to be delivered along the one or more fluid pathways. This can allow for the controlled transferring of fluids and/or materials between chambers and syringes. The outer surface of the shuttle valve 170 can include one or more recesses, which can provide secure positioning of a sealing feature 155 (such as an o-ring) that can assist with containing and directing fluid and material flow (such as by preventing unwanted fluid and/or material flow along the transfer line). Movement of the shuttle valve 170 along the transfer line 136 can be controlled by either the processing device 102 (such as via the motor 112) or manually (such as via the user pushing an end of the shuttle valve 170). The shuttle valve 170 can also include one or more internal valves 177 (such as passive one-way valves) that assist with controlling the direction of fluid and/or material flow through the shuttle valve 170.

Figure 7B:
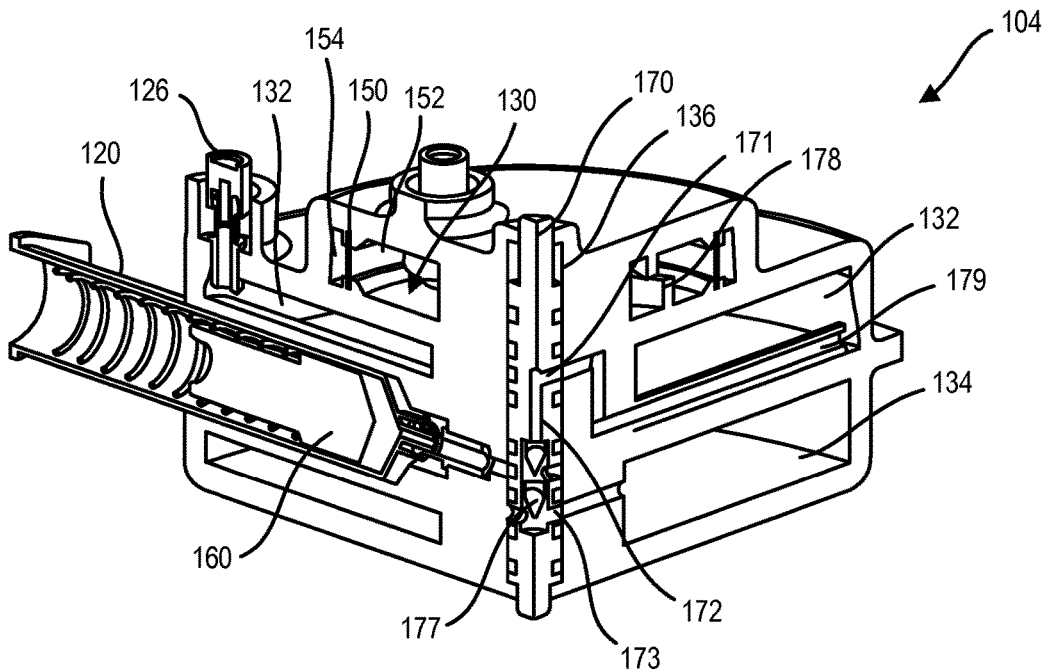
FIG. 7B is a perspective view of a section of the containment device of FIG. 4 showing the shuttle valve positioned in the transfer line such that the transfer pathway creates a fluid pathway between the second chamber and the third chamber.

As shown in FIG. 7B, the shuttle valve 170 can align its transfer pathway 172 such that the contents of the first chamber 130 can be in fluid communication with the third chamber 134. For example, a pathway can be crated between the two chambers as a result of the shuttle valve 170 aligning a first opening 171 of its transfer pathway 172 with a fluid pathway extending from the first chamber 130 and a second opening 173 of its transfer pathway 172 with a fluid pathway extending from the third chamber 134, as shown in FIG. 7B. Changes in rotation of the containment device 104 and/or an applied vacuum in the fluid pathways of the containment device 104 can also assist with transferring contents from one chamber to another.

In some implementation of the containment device, as shown in FIGS. 7A and 7B, the first chamber 130 can include turbulence features 178 that can assist with mixing contents within the first chamber 130. The turbulence features 178 can be passive, such as extruded features that extend into the chamber and act against the contents of the chamber, such as during agitation and/or centrifugation. In some implementations, the turbulence features 178 can be active, such as by providing mixing or turbulence of the contents of the chambers independent of movement of the containment device 104 (e.g., mixers, blenders, etc.). The turbulence features 178 can assist with breaking up, mixing, inducing agitation, and/or inducing turbulence of the contents in a respective chamber. In addition, any one of the chambers can include a siphon 179 that can assist with drawing out fluid and/or material from the chamber, such as in order to transfer such fluid and/or material to another chamber or syringe.

The SVF system 100 can provide a number of functions and can be used to process a variety of tissues and fluids. For example, the SVF system 100 can be used to process fat tissue that has been extracted from a patient in order to collect viable stem cells from the fat tissue, which can then be either stored for later use or subsequently implanted (e.g., injected) into a patient. The SVF system 100 can maintain a sterile environment within at least the containment device 104 such that the stem cells and even the remaining fat cells can be used for re-introduction into a patient. The SVF system 100 can also collect waste material in the containment device 104. This can allow for safe containment and disposal of any waste material. As such, once the desired cells and/or fluids have been collected from the containment device 104, the containment device 104, along with any unwanted contents (i.e., waste material) can be disposed of. Any subsequent use of the SVF system 100 can be done using a new (and sterile) containment device 104 that can be inserted and coupled to the reusable processing device 102 of the SVF system 100.

FIGS. 8A-8I diagrammatically illustrate a process of treating tissue cells using the SVF system 100 to collect stem cells in the syringe 120 of the containment device 104, such as for subsequent use. These figures also show examples of various fluid pathways that can be created within the containment device 104, such as resulting from the shuttle valve 170 (having a transfer pathway 172) moving along the transfer line 136, which can allow for various transfers of fluid and/or material within the containment device 104.

Figure 8A:
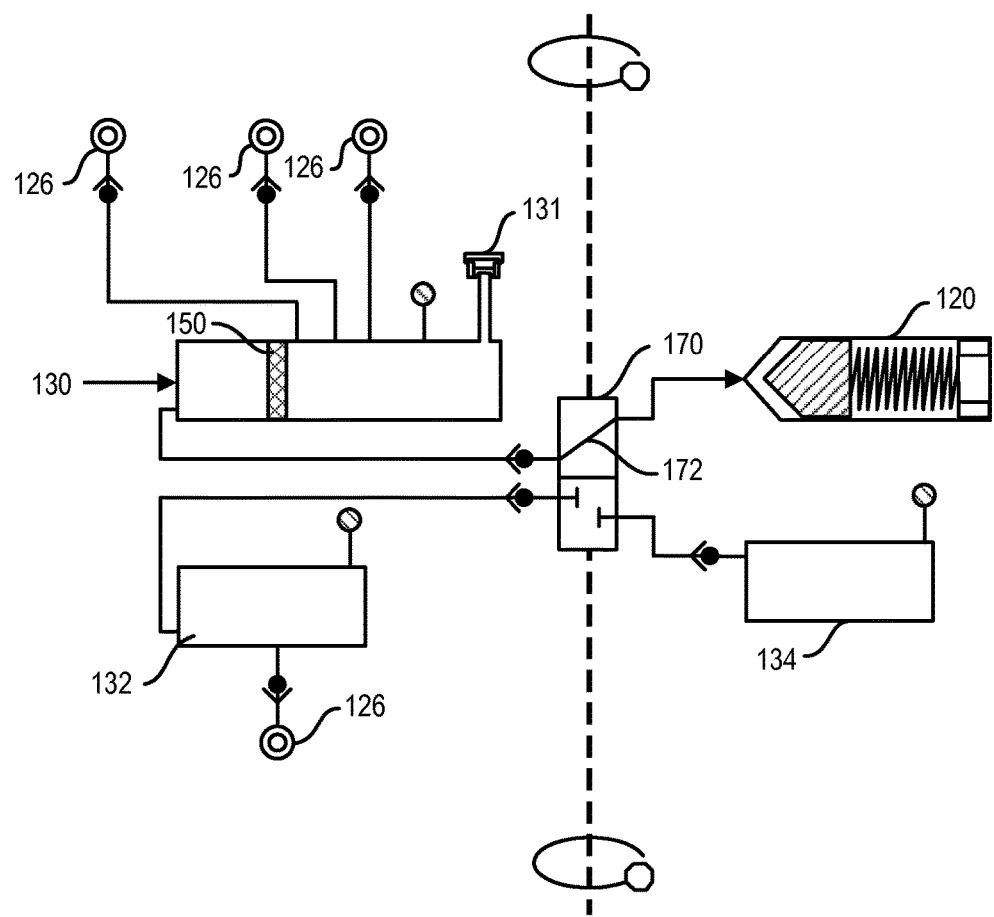
FIGS. 8A-8I diagrammatically illustrate a tissue processing method using an embodiment of the SVF system, such as the SVF system of FIG. 1.

FIG. 8A shows the first chamber 130, which can be used to collect fat tissue for processing. At least one port 126 can be in communication with the first chamber 130 in order to allow the addition of the fat cells, as well as other solvents, such as collagenase and dextrose into the first chamber 130. In addition, any one of the ports 126 can have a valve (e.g., passive or active valve) adjacent the port 126, which can assist with controlling the direction of fluid and material flow through the port 126, as well as assist with providing a sterile barrier. The first chamber 130 can also include a removal port 131, which can allow for the removal of remaining tissue in the first chamber 130. The second chamber 132 can be used to collect a rinsing agent, such as saline. The third chamber 134 can collect waste and the syringe 120 can collect stem cells that are extracted from the fat cells, as will be described in greater detail below.

Figure 8B:
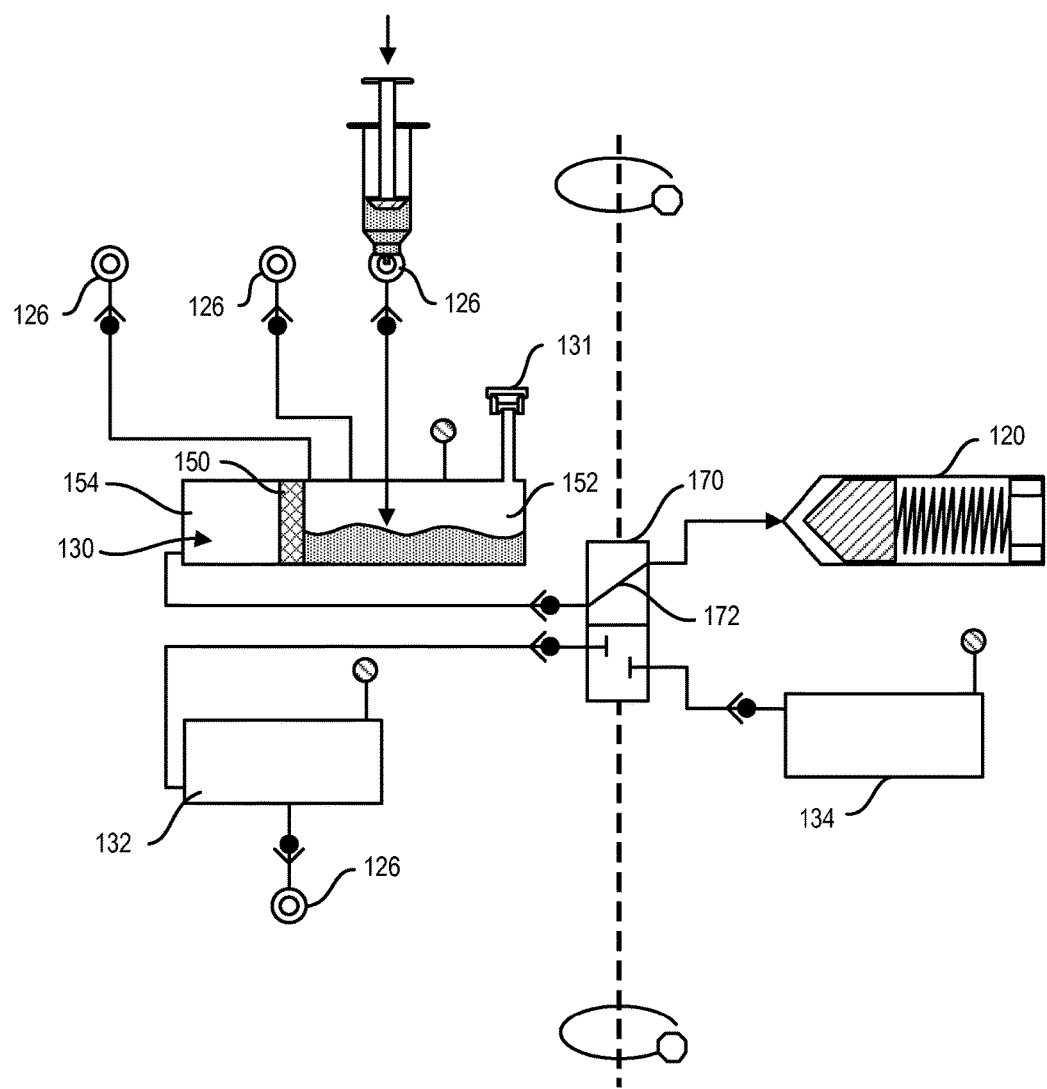
Figure 8C:
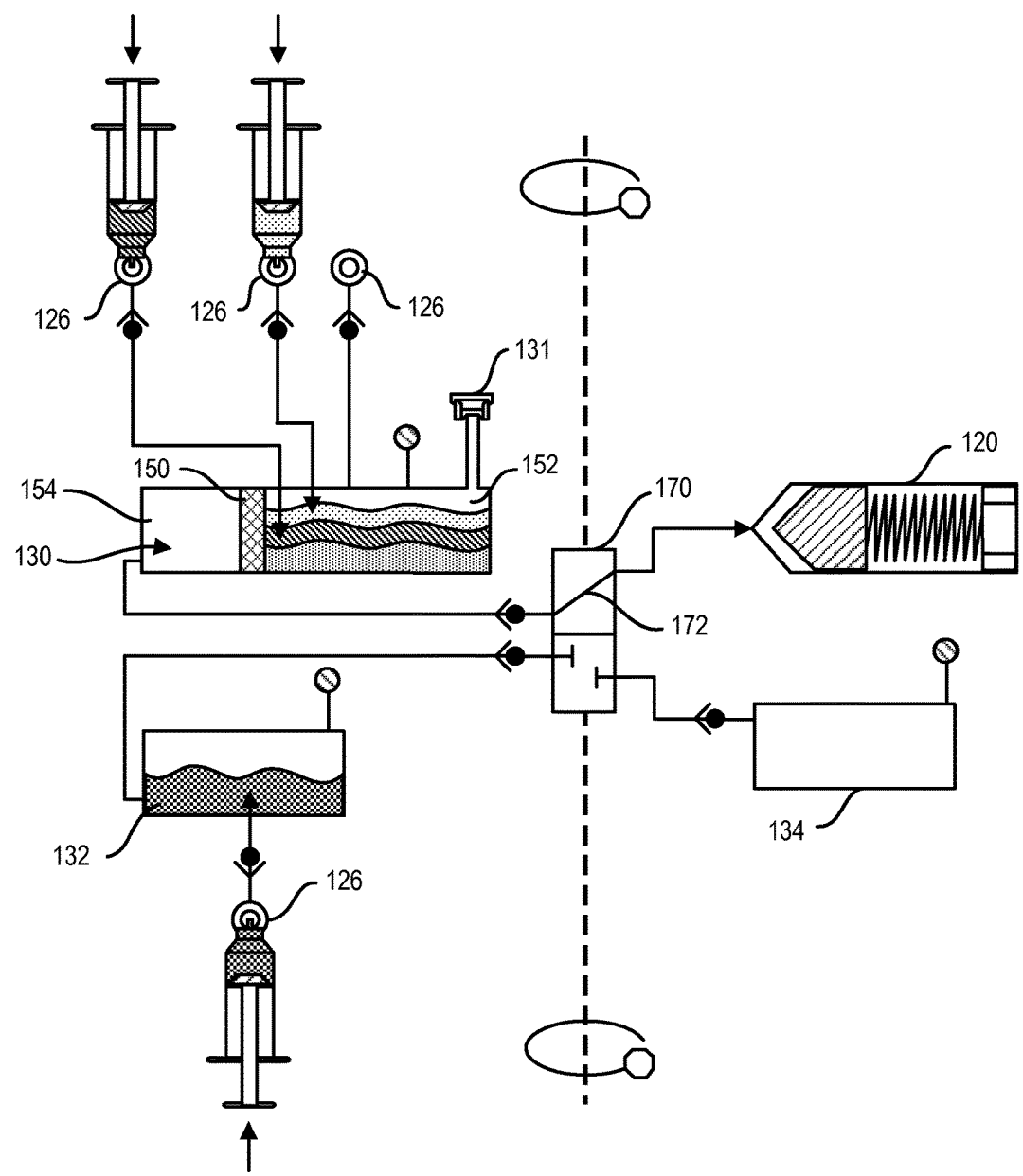

FIG. 8B shows the loading of fat tissue into the first chamber 130 through a port 126. Any of the ports 126 can include a one-way valve, which can assist with maintaining a sterile environment in the first chamber 130. The fat tissue can be loaded into the first sub-chamber 152 of the first chamber 130, with the first sub-chamber 152 being separated by the second sub-chamber 154 by a filter 150. In addition, the tissue can be loaded while the containment device is not moving (such as not rotating, etc.). As shown in FIG. 8C, additional solvents can be introduced into the first chamber 130 via one or more ports 126, such as into the first sub-chamber 152, such as dextrose and collagenase. Additionally, a saline solution can be introduced into the second chamber 132 via port 126, as also shown in FIG. 8C. The loading of the solvents and solutions can be also done while the containment device is not moving. Alternatively or in addition, the tissue and/or solvents and solutions can be added to the containment device while moving.

The loading of the tissue and/or solvents can be done either prior to or after the loading of the containment device 104 into the processing device 102. For example, the containment device 104 can be loaded with tissue and fluids in a sterile room, and then transported into a non-sterile room for processing. Even while in the non-sterile room, the contents of the containment device 104 can remain sterile as long as they remain within the containment device 104. This can allow for the SVF system 100 to be used in a variety of places, such as in doctor's offices, while still being able to process and collect fluids and/or material that have not been contaminated.

Figure 8D:
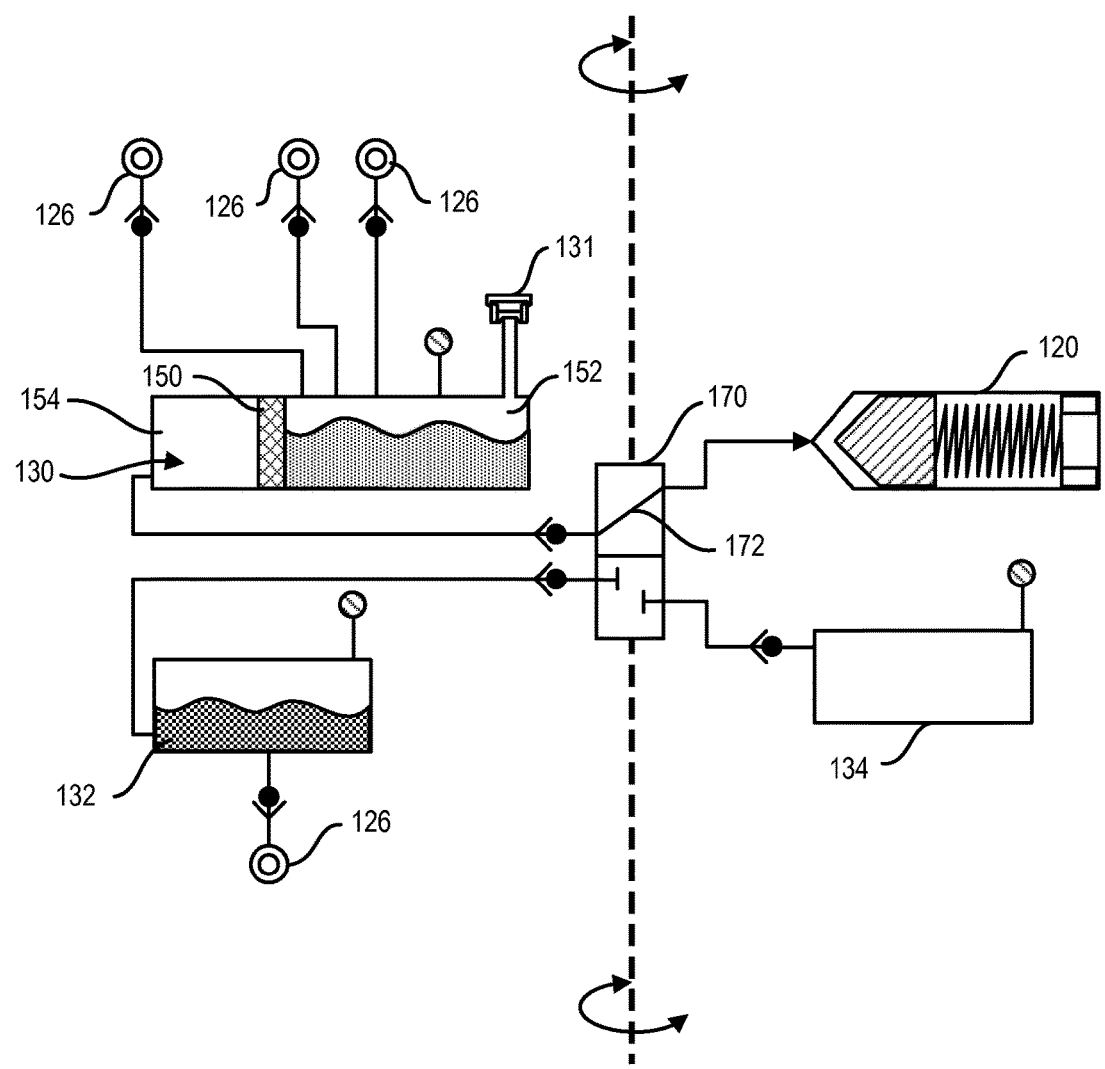
Figure 8E:
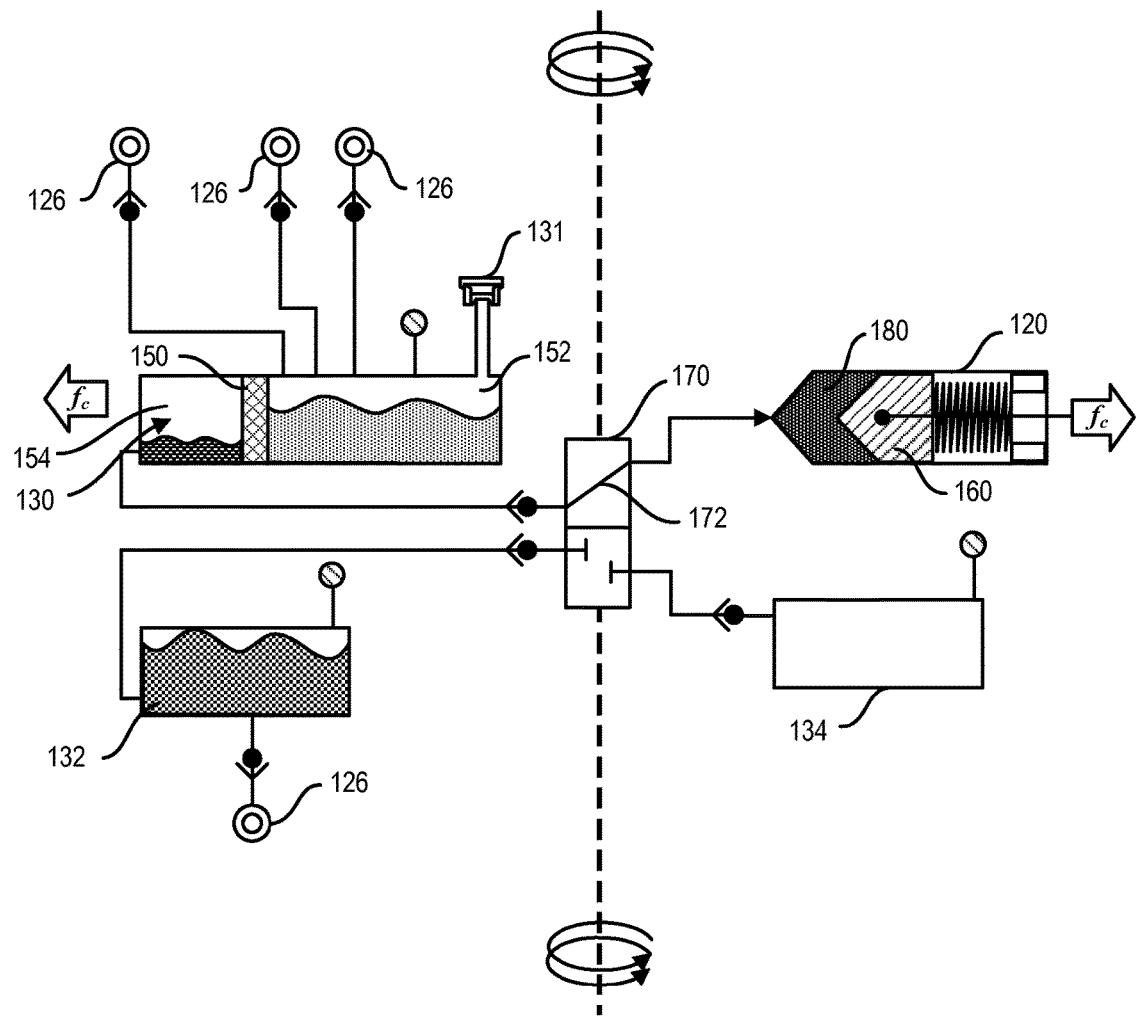

FIG. 8D shows the contents of the containment device 104 being agitated, such as by moving the containment device 104 back and forth along the center axis of the containment device, as shown with the arrows in FIG. 8D. Agitation of the contents in the containment device 104 can assist with mixing the contents within one or more chambers, such as the fat tissue and solvents in the first chamber 130. After a period of agitation, which can be controlled by the processing device 102, the containment device 104 can undergo centrifugation along the center axis of the containment device, such as shown with the double arrows in FIG. 8E, which can again be controlled by the processing device 102. During centrifugation, the contents in the first sub-chamber 152 of the first chamber 130 can be pushed distally towards the filter 150 as a result of centrifugal forces. As discussed above, the filter 150 can be configured to prevent and allow various fluids and/or materials to pass. In some implementations, the filter 150 can allow stem cells to pass. As shown in FIG. 8E, stem cells 180 are allowed to pass through the filter 150 and collect in the second sub-chamber 154.

In addition, as shown in FIG. 8E, either before or during centrifugation, the shuttle valve 170 can align its transfer pathway 172 to create a fluid pathway between the first chamber 130 and the syringe 120. As such, during centrifugation when the plunger 160 of the syringe 120 is retracted into the distal position, a vacuum can be created in this fluid pathway, which can force the stem cells from the first chamber 130 to the syringe 120. The processing device 102 can continue to rotate the containment device 104 in order to allow a desired amount of stem cells 180 to be collected in the syringe 120.

Figure 8F:
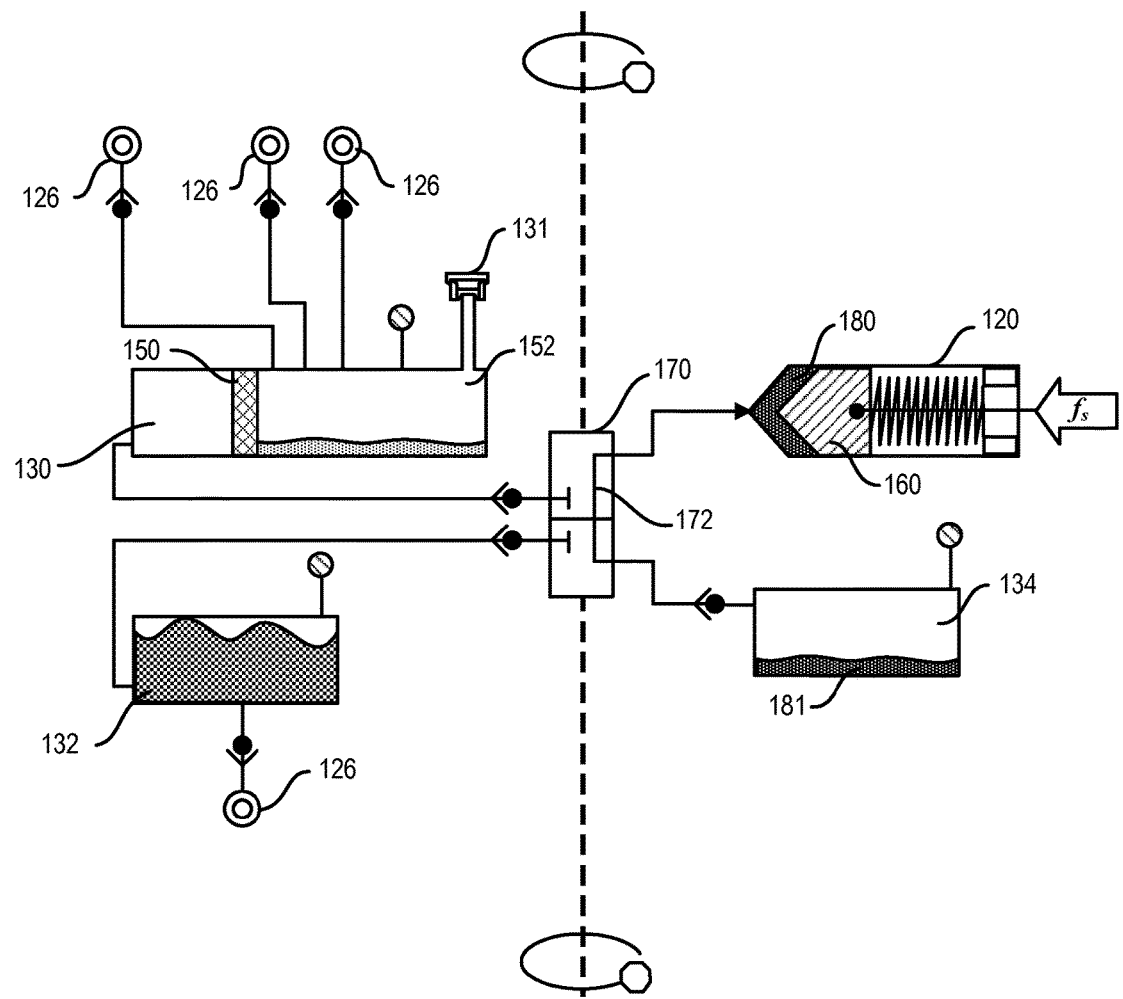

As shown in FIG. 8F, once the stem cells 180 have been collected by the syringe 120, the shuttle valve 170 can move along the transfer line 136 in order to create a fluid pathway between the syringe 120 and the third chamber 134 (i.e., waste chamber). In addition, the processing device 102 can slow down and stop rotation of the containment device 104. As the containment device 104 slows and eventually stops rotating, the plunger 160 of the syringe 120 is allowed to return to the proximal position. As the plunger 160 returns to the proximal position, the plunger 160 pushes out a portion of the contents collected in the syringe 120. In some implementations, the contents that are pushed out of the syringe 120 can be substantially waste material 181, which can be lighter in weight and smaller in mass and therefore more closely positioned to the outlet of the syringe 120 (compared to the stem cells that are heavier and positioned closer to the plunger 160).

Figure 8G:
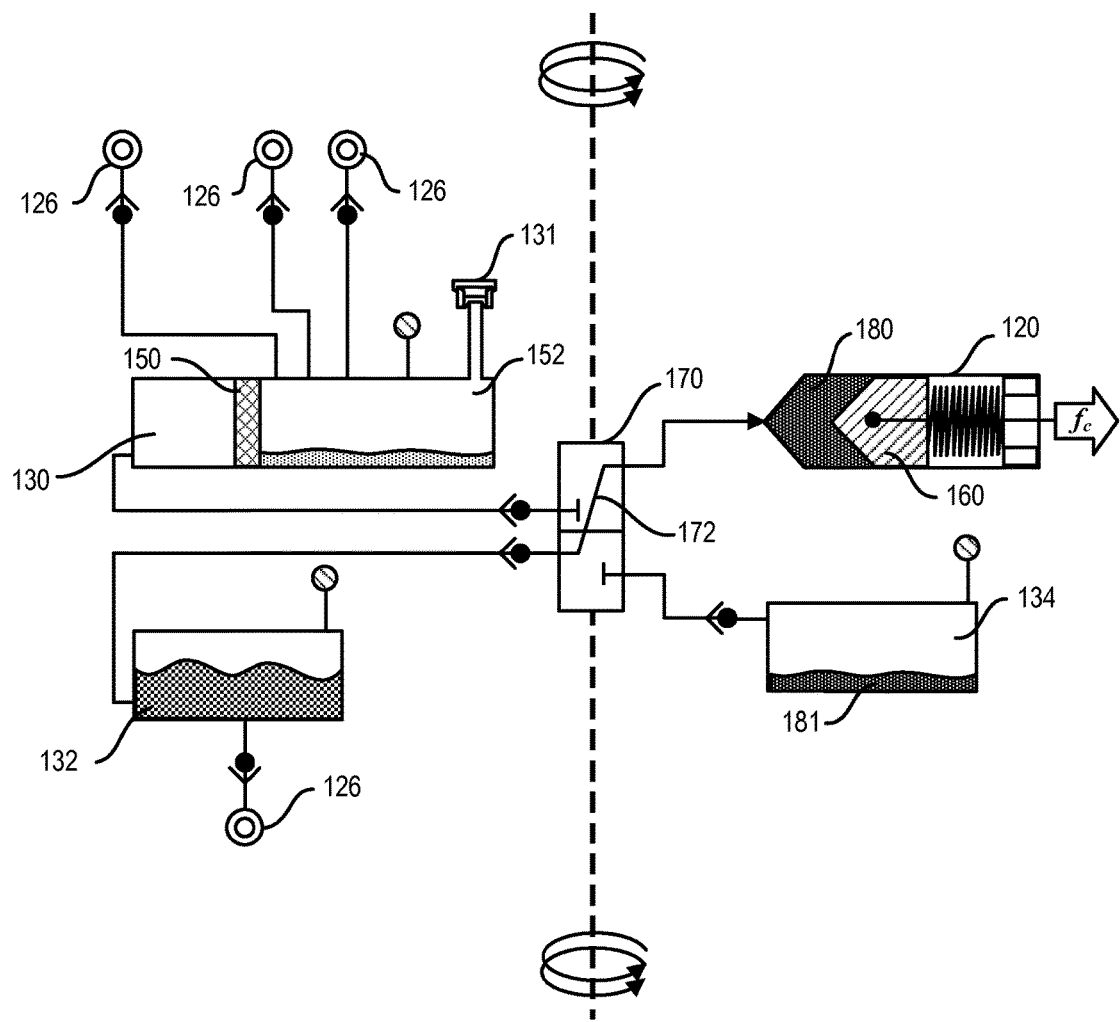

As shown in FIG. 8G, a rinse cycle can be performed by moving the shuttle valve 170 along the transfer line 136 to form a fluid pathway between the second chamber 132 and the syringe 120. The processing device 102 can centrifuge the containment device 104, as shown with the double arrows in FIG. 8G, in order to again cause the plunger 160 to retract towards the distal position thereby creating a vacuum and pulling solvent from the second chamber 132 into the syringe 120. This can allow the contents of the syringe to be washed, such as with saline.

Figure 8H:
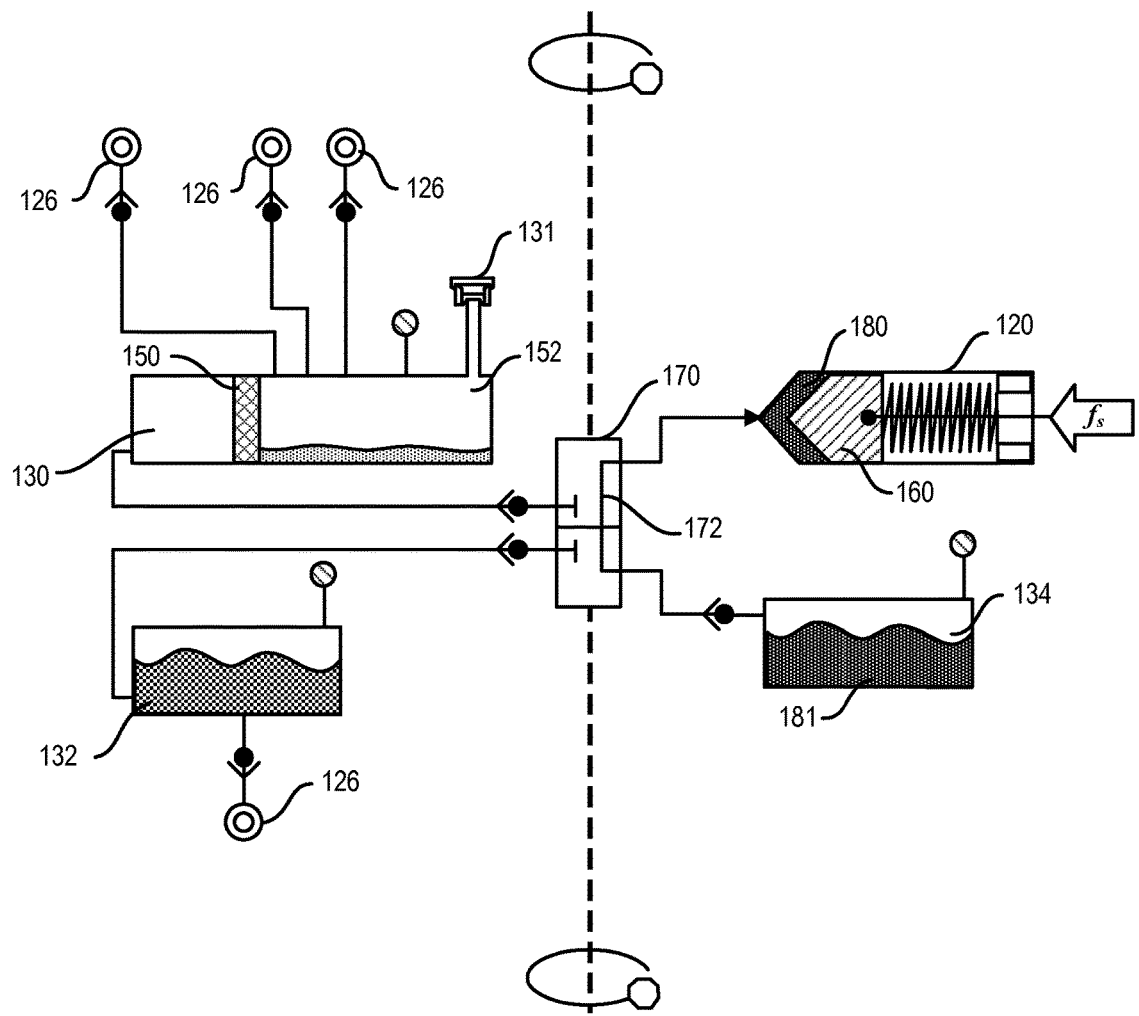

As shown in FIG. 8H, the shuttle valve 170 can again move along the transfer line 136 in order to create a fluid pathway between the syringe 120 and the third chamber 134 (i.e., waste chamber). In addition, the processing device 102 can slow down and stop rotation of the containment device 104. As the containment device 104 slows and eventually stops rotating, the plunger 160 of the syringe is allowed to return to the proximal position. As the plunger 160 returns to the proximal position, the plunger 160 pushes out a portion of the contents collected in the syringe 120. In some implementations, the contents that are pushed out of the syringe 120 can again be waste material from washing the stem cells 180. Again, contents in the syringe 120 that are lighter in weight and smaller in mass can be more closely positioned to the outlet of the syringe 120 (compared to the stem cells 180 that are heavier and positioned closer to the plunger 160) are, therefore, pushed into the third chamber 134. As such, the remaining contents in the syringe 120 can be the desired stem cells 180. The syringe 120 can be configured such that in the proximal position, there is a volume 184 that remains in the barrel of the syringe that is sufficient for containing a desired volume of stem cells 180.

Figure 8I:
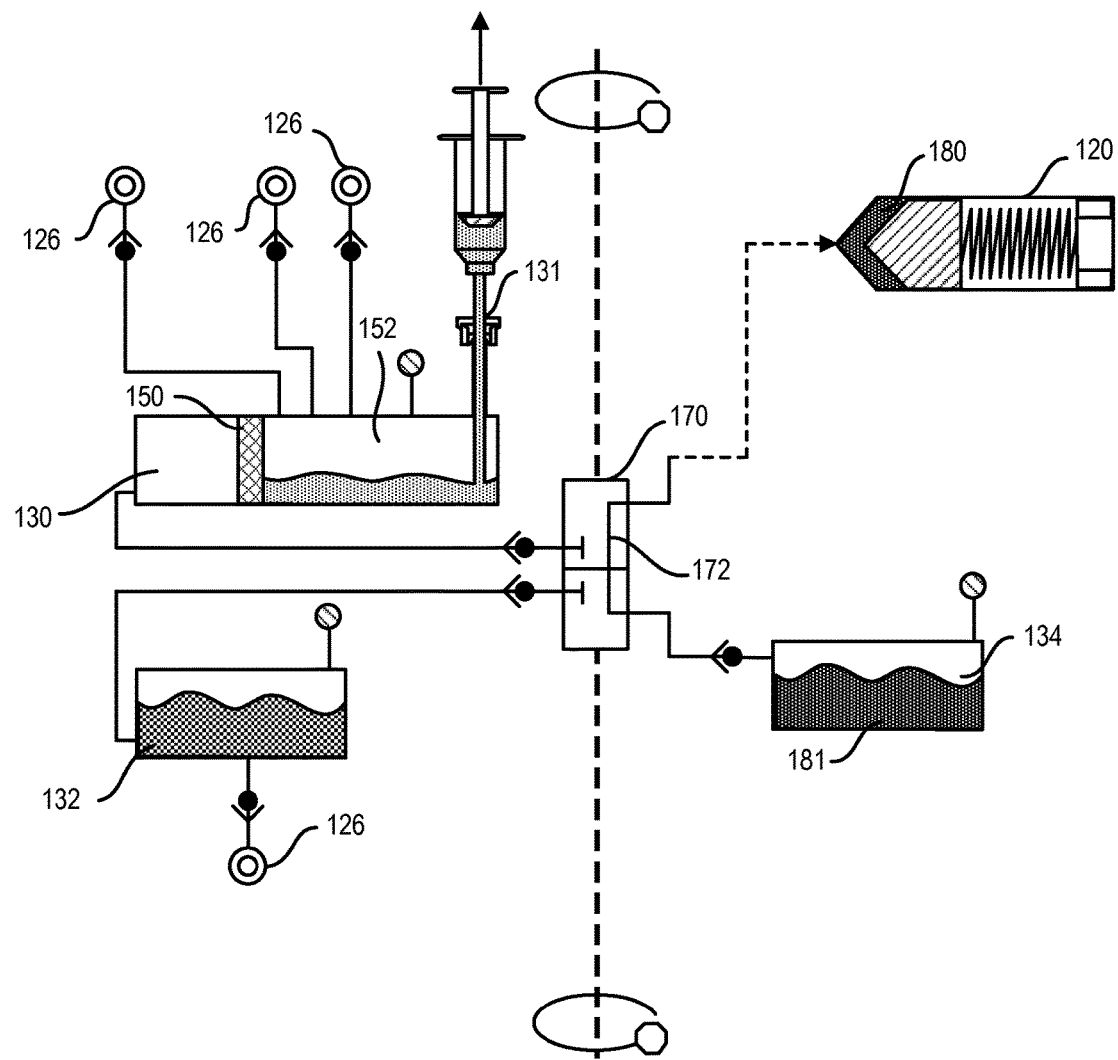
Figure 9:
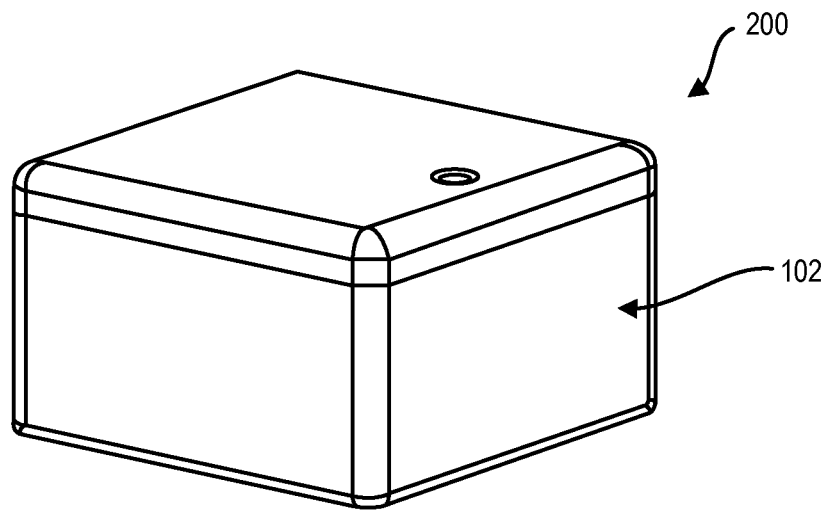
FIGS. 9-11 show another implementation of the SVF system, including a containment device and a processing device, with the containment device having an outer body that is fully enclosed and the containment device being releasably coupled to an inner compartment of the processing device.
Figure 10:
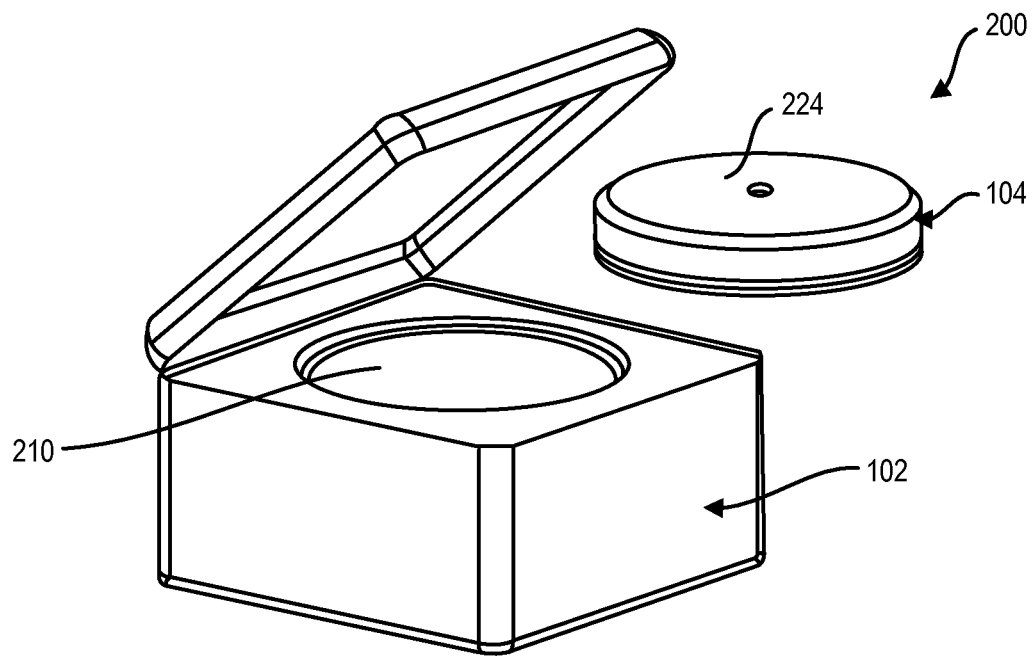

As shown in FIG. 8I, the syringe 120 containing the extracted and washed stem cells 180 can be removed from the containment device 104, such as for subsequent use. Any tissue remaining in the first sub-chamber 152 of the first chamber 130 can also be removed from the containment device 104, such as via the removal port 131. Neither the remaining tissue in the first chamber 130 nor the stem cells 180 have been contaminated during processing in the containment device 104. As such, both can be subsequently used, such as for re-introduction into a patient.

Furthermore, the containment device 104 along with its contents can be disposed of, thereby providing a safe and efficient way of disposing any byproduct and waste associated with the above process. As discussed above, a new and sterile containment device 104 can be used with the reusable processing device 102 for performing a subsequent tissue processing procedure.

Although the method above describes processing fat tissue for extracting and washing stem cells, any number of processes can be performed with the SVF system 100 using any number of solutions and/or materials, including any described herein. In addition, either the containment device 104 or the processing device 102 can be programmed to assist with any number of processes. For example, the SVF system 100 can include a control panel 190 (see, for example, FIGS. 1-3) that allows the user to program one or more processes for a tissue sample to undergo. In addition, the SVF system 100 can be programmed to monitor and detect one or more features associated with the contents of the SVF system 100, such as features associated with the collected stem cells 180 in the containment device 180. For example, one or more sensors 118 of the SVF system 100 can detect an amount of tissue collected in the first chamber 130. In addition, cells can be automatically detected and counted using an optical sensor of the SVF system, such as during various stages of processing (e.g., during centrifugation and washing). Measurements associated with the cell counting can be programmed by a user, which increase efficiency of the SVF system by halting processing when a desired cell density is reached. The cell counting method may be combined with a cell morphometry (quantifying cell size and shape, for example) to identify the presence and proportion of different types of cells being harvested.

FIGS. 9-13 show another implementation of the SVF system 200, including a containment device 204 and a processing device 202, with the containment device 204 that can be releasably coupled to an inner compartment 210 of the processing device 202. Any of the features and functions described above, such as with respect to the SVF system 100, can be included in the SVF system 200.

Figure 11:
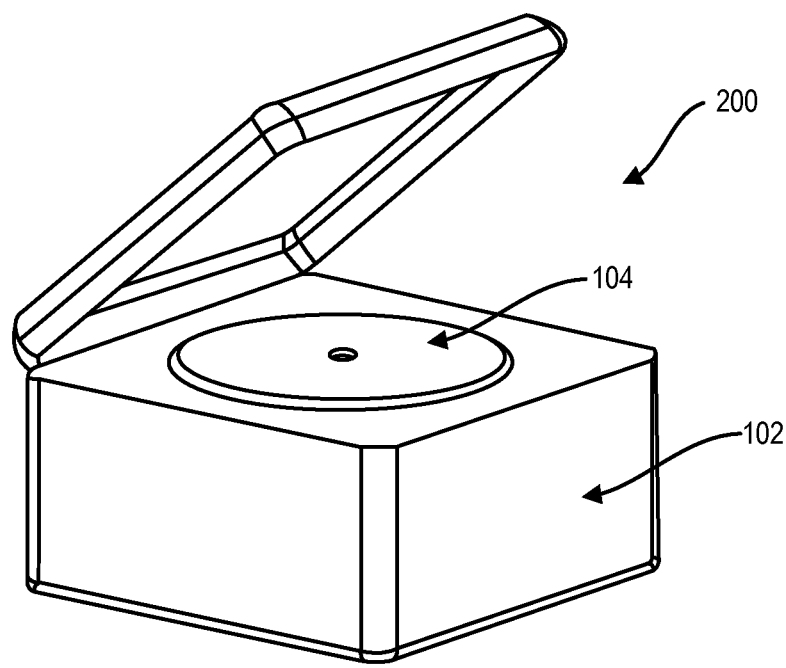
Figure 12:
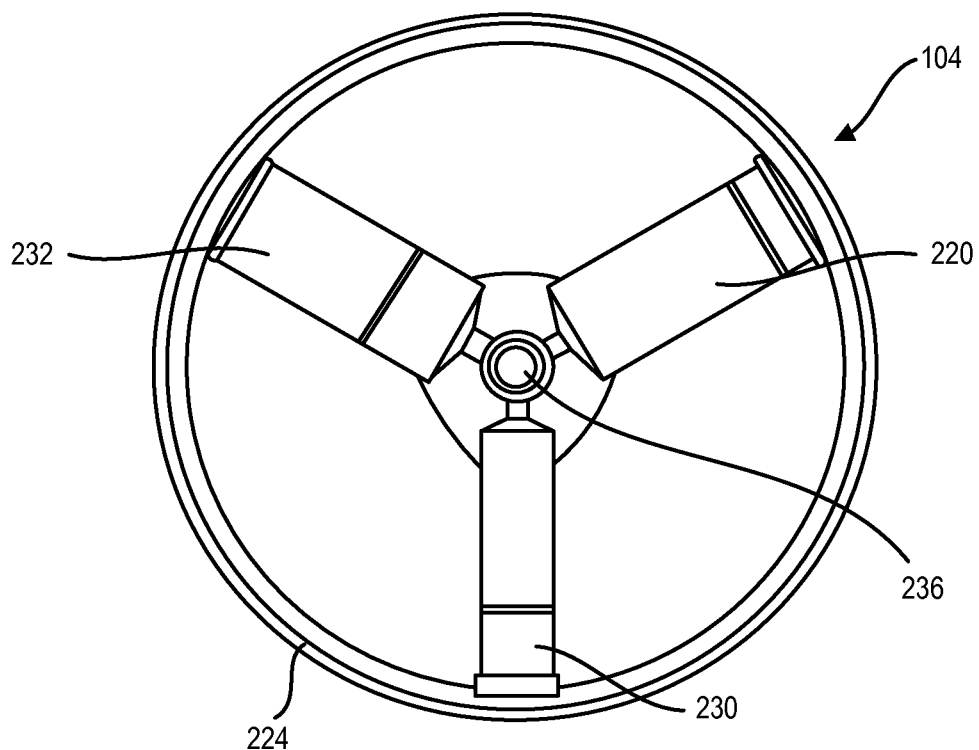
FIG. 12 is an open top view of the containment device of FIGS. 9-11 showing collection and delivery chambers evenly displaced radially about a transfer line that extends along a center axis of the containment device.
Figure 13:
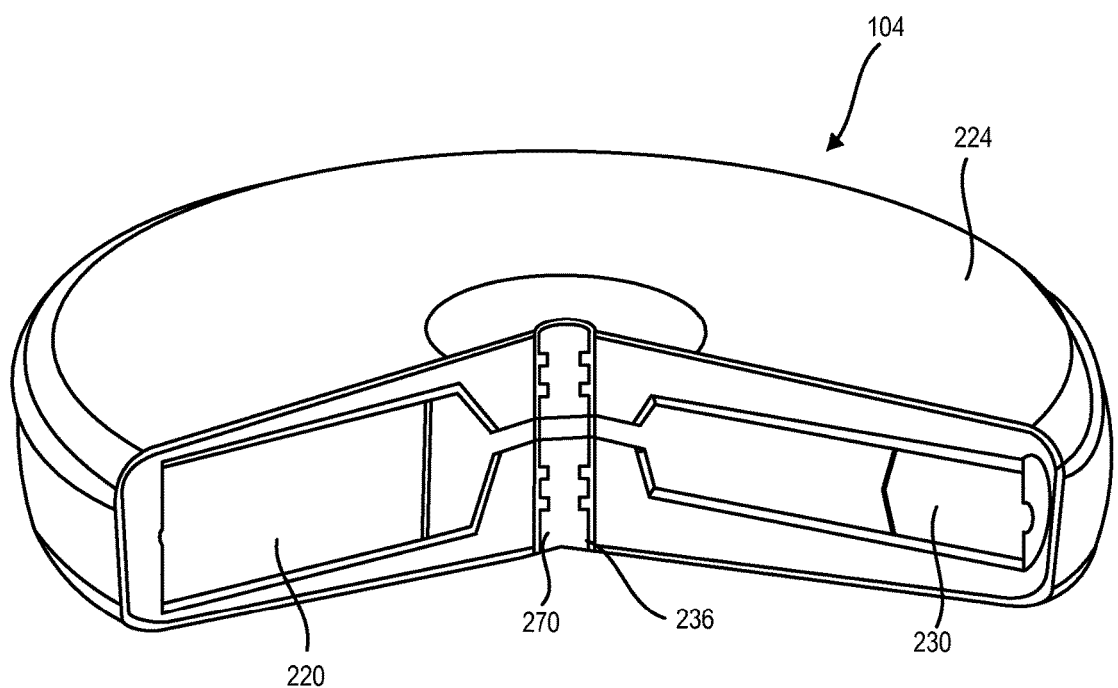
FIG. 13 is a perspective view of a section of the containment device of FIG. 12 showing a shuttle valve positioned along the transfer line.

As shown in FIGS. 11-13, the containment device 204 can have an outer body 224 that is fully enclosed. As such, the outer body 224 can be opened, such as to fill or remove one or more collection chambers or syringes (or syringe-like) 220, 230, 232 from within the outer housing 224. Any one of the collection chambers and/or syringes 220, 230, 232 can be in fluid communication with a transfer line 236, with can have the same or similar features and functions as the transfer line 136 described above.

As shown in FIG. 13, the transfer line 136 can include a shuttle valve 270, which can also include the same or similar features and functions as shuttle valve 170 described above. As such, the shuttle valve 170 can assist with transferring fluid and/or material between the collection chambers and/or syringes 220, 230, 232.

The fully enclosed housing 224 of the containment device can provide closed environment within the containment device, which can further assist with maintaining sterility and preventing contamination within the containment device. The fully enclosed housing can also provide a compact configuration of the containment device, which can be beneficial for storage and disposal of the containment device.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. A tissue processing system comprising:
   a processing device including an outer housing that contains an inner compartment; and
   a containment device that includes an outer body that releasably couples to the inner compartment of the processing device, the containment device comprising
      a transfer line that includes a hollow passageway that extends a distance along a center axis of the outer body;
      at least one chamber in fluid communication with the transfer line and positioned within the outer body;
      a collection chamber releasably coupled to a collection port contained within the outer body, the collection chamber being in fluid communication with the transfer line; and
      a shuttle valve including a transfer pathway that extends through the shuttle valve, the shuttle valve being moveable along the transfer line for creating, depending upon a position of the shuttle valve along the transfer pathway, a fluid pathway between two chambers of the at least one chamber or between a chamber of the at least one chamber and the collection chamber.

2. The tissue processing system of claim 1, wherein the containment device includes a first chamber of the at least one chamber, the first chamber having a filter that partitions the first chamber into a first sub-chamber and a second sub chamber.

3. The tissue processing system of claim 2, wherein the first sub-chamber is positioned closer to the center axis than the second sub-chamber.

4. The tissue processing system of claim 2, wherein the second sub-chamber is in fluid communication with the transfer line.

5. The tissue processing system of claim 2, wherein the first sub-chamber is in fluid communication with a port that extends through the outer body.

6. The tissue processing system of claim 5, wherein the port is coupled to a tissue collection device.

7. The tissue processing system of claim 2, wherein the second sub-chamber is in fluid communication with the collection chamber when the shuttle valve is positioned along the transfer line such that the transfer pathway is in fluid communication with the second sub-chamber and the collection chamber.

8. The tissue processing system of claim 2, wherein the filter allows the passage of stem cells and prevents the passage of fat tissue through the filter.

9. The tissue processing system of claim 1, wherein the shuttle valve includes a passive valve along the transfer pathway that controls the direction of fluid or material through the shuttle valve.

10. The tissue processing system of claim 1, wherein the first chamber includes at least one of a passive feature and an active feature for at least one of breaking-up, mixing, inducing turbulence, and inducing agitation to contents contained in the first chamber.

11. The tissue processing system of claim 1, wherein at least one of the collection chamber, the one or more chambers, and the transfer pathway includes a surface coating that influences the retention or rejection of at least one of a specific chemical and a specific biological material.

12. The tissue processing system of claim 1, wherein the collection chamber includes a plunger and a spring that applies a spring force against the plunger.

13. The tissue processing system of claim 12, wherein the spring force is less than a centrifugal force of the plunger when the containment device rotates during centrifugation thereby allowing the plunger to compress the spring and create a vacuum in the collection chamber.

14. The tissue processing system of claim 13, wherein the vacuum forces contents into the collection chamber from one or more of the at least one chamber and the collection chamber depending upon the position of the shuttle valve.

15. The tissue processing system of claim 12, wherein the processing device includes a sensor that collects sensed data, and wherein the processor processes the sensed data for determining a processing feature of the containment device during the one or more tissue processes.

16. The tissue processing system of claim 15, wherein the processor processes the sensed data in real-time.

17. The tissue processing system of claim 15, wherein the processing feature includes at least one of a rotational speed of the containment device, a rate of collection of sample tissue into the first sub-chamber, and a temperature in the containment device.

18. The tissue processing system of claim 1, wherein the processing device includes a control panel in communication with a processor for programming one or more tissue processes to be completed by the tissue processing system.

19. The tissue processing system of claim 1, wherein the collection chamber is a syringe.

20. A method comprising:
   allowing a coupling of a containment device of a tissue processing system to an inner compartment of a processing device of the tissue processing system;
   allowing a loading of a tissue sample and a solution in a first sub-chamber of a first chamber of the containment device, the first chamber including a filter that divides the first chamber into the first sub-chamber and a second sub-chamber;
   agitating the containment device to assist with mixing the tissue sample and the solution;

moving a shuttle valve positioned along a transfer line that extends a distance within an outer body of the containment device, the shuttle valve including a transfer pathway that extends through the shuttle valve;

positioning the shuttle valve such that the transfer pathway creates a first fluid pathway between the second sub-chamber and a collection chamber releasably coupled to a collection port within the containment device;

rotating the containment device along a center axis of the containment device to centrifuge the tissue sample and solvent;

allowing a first type of cell comprising the tissue sample to pass through the filter and collect in the second sub-chamber; and creating, during rotation of the containment device, a vacuum in the collection chamber thereby drawing the first type of cells into a volume within the collection chamber, the vacuum created as a result of the rotation of the containment device.

21. The method of claim 20, further comprising positioning the shuttle valve such that the transfer pathway of the shuttle valve creates a second fluid pathway between a second chamber and the collection chamber;

rotating the containment device along the center axis of the containment device to create the vacuum in the collection chamber and draw a washing solution contained in the second chamber into the volume of the collection chamber;

positioning the shuttle valve such that the transfer pathway creates a third fluid pathway between the collection chamber and a third chamber; and stopping the rotation of the containment device thereby forcing a waste solution out of the collection chamber and into the third chamber and allowing the first type of cells to remain in the volume of the collection chamber.

22. The method of claim 21, further comprising allowing the removal of at least one of the containment device and the collection chamber from the processing device.

23. The method of claim 21, wherein the first type of cells include one or more of a stem cell, a progenitor cell, a stromal cell, a vascular cell, and an angiogenic cell.

24. The method of claim 20, wherein the creating the vacuum further includes allowing a plunger acting upon a spring in the collection chamber to overcome the spring force of the spring with a centrifugal force of the plunger thereby moving the plunger and compressing the spring.

25. The method of claim 20, wherein the first sub-chamber is positioned closer to the center axis than the second sub-chamber.

26. The method of claim 20, wherein the first sub-chamber is in fluid communication with a port that extends through the outer body.

27. The method of claim 26, wherein the port is coupled to a tissue collection device.

28. The method of claim 20, further comprising programming, based on an input from a control panel of the processing device, the tissue processing system to perform a tissue process on the tissue sample, wherein the processing device includes a processor in communication with the control panel.

29. The method of claim 28, further comprising processing, by the processor, sensed data collected by a sensor of the processing device and adjusting a processing feature of the containment device based on the processed sensed data.

30. The method of claim 29, wherein the processor processes the sensed data in real-time.

31. The method of claim 29, wherein the processing feature includes at least one of a rotational speed of the containment device, a rate of collection of the tissue sample into the first sub-chamber, and a temperature in the containment device.

* * * * *